(12) United States Patent
Rutschmann et al.

(10) Patent No.: US 10,098,665 B2
(45) Date of Patent: Oct. 16, 2018

(54) SPINE DEROTATION SYSTEM

(71) Applicant: Depuy Synthes Products, Inc., Raynham, MA (US)

(72) Inventors: Helmut Rutschmann, Weil am Rhein (DE); Madeleine Kaegi, Baden-Baden (DE)

(73) Assignee: DePuy Synthes Products, Inc., Raynham, MA (US)

( * ) Notice: Subject to any disclaimer, the term of this patent is extended or adjusted under 35 U.S.C. 154(b) by 173 days.

(21) Appl. No.: 13/804,254

(22) Filed: Mar. 14, 2013

(65) Prior Publication Data

US 2014/0039556 A1    Feb. 6, 2014

Related U.S. Application Data

(60) Provisional application No. 61/678,415, filed on Aug. 1, 2012.

(51) Int. Cl.
*A61B 17/70* (2006.01)
*A61B 90/00* (2016.01)

(52) U.S. Cl.
CPC ........ *A61B 17/7002* (2013.01); *A61B 17/708* (2013.01); *A61B 17/7077* (2013.01);
(Continued)

(58) Field of Classification Search
CPC . A61B 17/70; A61B 17/7049; A61B 17/7001; A61B 17/7002; A61B 17/7005;
(Continued)

(56) References Cited

U.S. PATENT DOCUMENTS 3,865,105 A    2/1975 Lode
4,005,883 A *  2/1977 Guest ........................... 285/322
(Continued)

FOREIGN PATENT DOCUMENTS

DE    8712943 U1    11/1987
DE    9112466       12/1991
(Continued)

OTHER PUBLICATIONS

International Search Report and Written Opinion, dated Feb. 6, 2014, received in connection with corresponding International Application No. PCT/US2013/053211.
(Continued)

*Primary Examiner* — Jacqueline Johanas
*Assistant Examiner* — Tessa Matthews
(74) *Attorney, Agent, or Firm* — Meunier Carlin & Curfman LLC

(57) ABSTRACT

A spine derotation system includes bone fixation elements, fixture members, clamps and stabilizers. The clamps can collectively lock together multiple proximal ends of bone fixation elements extending from one lateral side of the spine. The stabilizers may include clamp stabilizers that are configured to couple together two or more clamps to each other so as to facilitate derotation and alignment of multiple vertebrae of a patient's spine. The stabilizers may also include fixture stabilizers that are configured to couple together two fixture members on the same vertebra to facilitate derotation.

25 Claims, 21 Drawing Sheets

(52) U.S. Cl.
CPC ...... *A61B 17/7085* (2013.01); *A61B 17/7035* (2013.01); *A61B 2090/034* (2016.02)

(58) Field of Classification Search
CPC ............ A61B 17/7007; A61B 17/7008; A61B 17/705; A61B 17/7076; A61B 17/7077; A61B 17/708; A61B 17/7079; A61B 17/7085; A61B 17/7035; A61B 17/7086; A61B 17/7091; A61B 17/7011–17/7019
USPC .................................................. 606/246–278
See application file for complete search history.

(56) References Cited

U.S. PATENT DOCUMENTS

| | | |
|---|---|---|
| 5,219,349 A | 6/1993 | Krag et al. |
| 5,281,223 A | 1/1994 | Ray |
| 5,385,565 A | 1/1995 | Ray |
| 5,395,370 A | 3/1995 | Muller et al. |
| 5,478,340 A | 12/1995 | Kluger |
| 5,490,851 A | 2/1996 | Nenov et al. |
| 5,632,744 A | 5/1997 | Campbell, Jr. |
| 5,672,175 A | 9/1997 | Martin |
| 5,800,434 A | 9/1998 | Campbell, Jr. |
| 5,814,046 A | 9/1998 | Hopf |
| 5,849,012 A | 12/1998 | Abboudi |
| 6,090,113 A | 7/2000 | Le Couedic et al. |
| 6,090,133 A | 7/2000 | Richter et al. |
| 6,454,806 B1 * | 9/2002 | Cohen .................. A61F 2/4455 623/17.15 |
| 6,755,828 B2 | 6/2004 | Shevtsov et al. |
| 7,188,626 B2 | 3/2007 | Foley et al. |
| 7,655,008 B2 | 2/2010 | Lenke et al. |
| 7,658,753 B2 | 2/2010 | Carl et al. |
| 7,670,358 B2 | 3/2010 | Barry |
| 7,708,765 B2 | 5/2010 | Carl et al. |
| 7,776,072 B2 | 8/2010 | Barry |
| 7,794,464 B2 | 9/2010 | Bridwell et al. |
| 7,951,168 B2 | 5/2011 | Chao et al. |
| 7,951,175 B2 | 5/2011 | Chao et al. |
| 8,002,801 B2 | 8/2011 | Carl et al. |
| 8,007,516 B2 | 8/2011 | Chao et al. |
| 8,016,860 B2 | 9/2011 | Carl et al. |
| 8,043,345 B2 | 10/2011 | Carl et al. |
| 8,147,524 B2 | 4/2012 | Vallespir |
| 8,221,426 B2 | 7/2012 | Justis et al. |
| 8,221,474 B2 | 7/2012 | Bridwell et al. |
| 8,361,121 B2 | 1/2013 | Barry |
| 9,198,696 B1 * | 12/2015 | Bannigan ............ A61B 17/7052 |
| 2002/0173791 A1 | 11/2002 | Howland |
| 2003/0205075 A1 * | 11/2003 | Strippgen .............. B21D 11/06 72/173 |
| 2004/0024461 A1 * | 2/2004 | Ferree ........................ 623/17.13 |
| 2004/0172022 A1 | 9/2004 | Landry et al. |
| 2005/0245928 A1 | 11/2005 | Colleran et al. |
| 2006/0247649 A1 | 11/2006 | Rezach et al. |
| 2007/0213715 A1 * | 9/2007 | Bridwell et al. ................ 606/61 |
| 2007/0213716 A1 | 9/2007 | Lenke et al. |
| 2007/0225712 A1 * | 9/2007 | Altarac .............. A61B 17/7004 606/64 |
| 2007/0233079 A1 * | 10/2007 | Fallin et al. ..................... 606/61 |
| 2007/0239161 A1 * | 10/2007 | Giger et al. ..................... 606/61 |
| 2008/0154279 A1 * | 6/2008 | Schumacher et al. ......... 606/104 |
| 2008/0172062 A1 * | 7/2008 | Donahue et al. ............. 606/104 |
| 2008/0294206 A1 | 11/2008 | Choi et al. |
| 2009/0216237 A1 | 8/2009 | Frezal et al. |
| 2009/0228051 A1 | 9/2009 | Kolb et al. |
| 2010/0042149 A1 * | 2/2010 | Chao .................. A61B 17/7077 606/246 |
| 2010/0312281 A1 | 12/2010 | Barry |
| 2010/0318129 A1 | 12/2010 | Seme et al. |
| 2010/0324610 A1 | 12/2010 | Bridwell et al. |
| 2011/0106082 A1 * | 5/2011 | Kave et al. ..................... 606/70 |
| 2011/0172714 A1 * | 7/2011 | Boachie-Adjei ... A61B 17/7086 606/264 |
| 2012/0035659 A1 * | 2/2012 | Barrus ............... A61B 17/7049 606/251 |
| 2012/0203279 A1 | 8/2012 | Walters et al. |
| 2013/0211453 A1 * | 8/2013 | Lenke .................. A61B 17/708 606/250 |

FOREIGN PATENT DOCUMENTS

| | | |
|---|---|---|
| DE | 4127303 A1 | 2/1993 |
| DE | 10101478 | 7/2002 |
| DE | 10125717 A1 | 12/2002 |
| EP | 0528177 B1 | 2/1993 |
| EP | 1392190 B1 | 3/2004 |
| FR | 2722393 A1 | 1/1996 |
| JP | 10248855 A | 9/1998 |
| JP | 200350731 A | 12/2000 |
| WO | 9002527 A1 | 3/1990 |
| WO | 9844858 A1 | 10/1998 |
| WO | 02094114 A1 | 11/2002 |
| WO | 2009/132110 | 10/2009 |
| WO | 2012/034005 | 3/2012 |

OTHER PUBLICATIONS

Smith, William, et al., "XLP™ Surgical Technique," Maximum Access Surgical Platform, NuVasive® Creative Spine Technology®, 2007, 24 pages.

Cotrel, "New Universal Instrumentation in Spinal Surgery", New Spinal Instrumentation, Clinical Orthopaedics and Related Research, 1998, No. 227. pp. 10-23.

Dick, Jeffrey C., Mechanical Evaluation of Cross-Link Designs in Rigid Pedicle Screw Systems, SPINE, vol. 22, No. 4, 1997, pp. 370-375.

Lee, Direct Vertebral Rotation: A New Technique of Three-Dimensional Deformity Correction With Segmental Pedicle Screw Fixation in Adolescent Idiopathic Scoliosis, SPINE, vol. 29, No. 3, pp. 343-349, 2004.

Liu, Biomechanical Evaluation of a Central Rod System in the Treatment of Scoliosis, Clinical Biomechanics, Vo. 13, pp. 548-559, 1998.

Mohan, History of Surgery for the Correction of Spinal Deformity, Neurosurg Focus, Vo. 14, No. 1, 2003, pp. 1-5.

Suk et al., "Comparison of Cotrel-dubousset pedicle screws and hooks in the treatment of idiopathic scoliosis." International Orthopaedics 18(6):341-6 1994.

* cited by examiner

SPINE DEROTATION SYSTEM

RELATED APPLICATIONS

This application claims the benefit of U.S. Provisional Application No. 61/678,415 filed Aug. 1, 2012 and hereby incorporated herein in its entirety by reference.

BACKGROUND

It is often necessary, due to various spinal disorders, to surgically correct and stabilize spinal curvatures, or to facilitate spinal fusion through an open approach or through a minimally invasive approach. Numerous systems for treating spinal disorders have been disclosed. One known method involves a pair of elongated members, typically rods, longitudinally fixed to the posterior spine on either side of spinous processes of the vertebral column. Each rod is attached to various vertebrae along the length of the spine by engaging bone fixation elements to the vertebra and fixing a rod to the bone fixation elements. The bone fixation elements commonly include a U-shaped rod-receiving channel for receiving the rod therein. Moreover, the rod-receiving channel often interacts with a locking cap to clamp and fix the position of the rod with respect to the bone fixation element.

Surgeons may have difficulty aligning the rod(s) within the rod-receiving channels formed in the body of the bone fixation elements. For example, the body of the bone fixation elements may be out of vertical and/or horizontal alignment with one another due to the curvature of the spine or the size and shape of each vertebra.

Thus, it is desirable to construct an apparatus to facilitate insertion of the longitudinal rods into the rod-receiving channels formed in the bone fixation elements and to derotate the spine.

SUMMARY

Implementations of the present disclosure overcome the problems of the prior art by providing a stabilizer for a spine derotation system. The spine derotation system includes a first and second fixture members. Each of the fixture members includes a distal end configured for attachment to a vertebra and a proximal end configured to extend from the vertebra. The stabilizer includes a first end, a second end and a body. The first end is configured to connect to the proximal end of the first fixture member. The second end is configured to connect to the proximal end of the second fixture member. The body extends between the first and second ends and is configured to couple motion of the proximal ends, such as translation, of the fixture members.

The stabilizer may include the additional components below either collectively, additively, providing further details to a component already introduced, or as isolated alternatives.

For example, the stabilizer first end may include a first opening configured to fit over the proximal end of the first fixture member. The second end may also include a second opening configured to fit over the proximal end of the second fixture member. The first and second openings, for example, may be cylindrical openings. The first and second handles may be configured to connect to the first and second openings via threaded connections.

The first and second ends may be pivotally coupled to the body. Also, the body may have an adjustable length or be configured to lengthen. For example, the body may include two members. One of the members is configured to slide within another one of the members so as to lengthen or shorten the body. An optional lock mechanism may be configured to alternatively stop and allow relative sliding of the two members.

The stabilizer may further include at least a first handle that's configured to connect to and extend from the first end. A second handle may also be included. The second handle is configured to connect to and extend from the second end. When both handles are used, they may extend laterally away from each other.

In another implementation, each of the first and second handles may include a shaft and each of the first and second ends may include a handle receptacle. The shaft may be configured to extend through the handle receptacle and lock against one of the first or second fixtures.

Also, in another implementation, the stabilizer, first fixture member and second fixture member may be configured to form a triangle when connected together and attached to the vertebra.

In yet another implementation, the first end may be configured to connect to the proximal end of the first fixture member using a first male-female connection. The second end may also be configured to connect to the proximal end of the second fixture member using a second male-female connection. Each of the first and second male-female connections may include a split male member. The split male member may include a shaft ending in an enlarged end.

Also, the first and second end may be connected to the body via a pivot joint. For example, the pivot joint may include a ball-and-socket joint. Each of the first and second ends may include a ball of the ball-and-socket joint. And, the body may include a pair sockets. Each of the sockets may be configured to receive the ball of each of the first and second ends. The sockets, for example, may be defined between a pair of plates of the body.

The body may further include a fastener for securing the pair of plates in a parallel relationship such as by transfixing the plates. The body may also include a bias mechanism, such as a coil spring extending around the fastener, configured to urge the plates together. The fastener may be configured to hold a minimum space between the plates less than a diameter of the ball of the ball-and-socket joint.

In another implementation, the spine derotation system may further include a plurality of first fixture members and a plurality of second fixture members. A first clamp is configured to connect the proximal ends of the first fixture members. A second clamp is configured to connect the proximal ends of the second fixture members. The stabilizer first end is configured to connect to the first clamp. Also, the stabilizer second end is configured to connect to the second clamp.

When used with the fixture members, the split male member of the first end may be configured to engage an opening of the first clamp. And, the split male member of the second end may be configured to engage an opening in the second clamp. Also, the first and second clamps may include a plurality of openings configured to receive the split male member. The first and second clamps may also include a pair of parallel arms configured to open and close around the proximal ends of the first and second fixture members.

In another implementation, the distal end of the first fixture member may be configured to attach to a first pedicle screw and the distal end of the second fixture member may be configured to attach to a second pedicle screw.

In another implementation, the first and second fixture members may extend away from the vertebra at a diverging angle.

The first and second ends may also include inward flanges configured to stop sliding of the first and second ends relative to the fixture members.

The first opening may be configured to allow passage of a driver through the first end. This allows access to a locking cap at the distal end of the first fixture member.

A method of derotating the spine includes attaching first and second fixture members to a vertebra of the spine. The method includes connecting the first end of the stabilizer to a proximal end of the first fixture member. The method includes connecting a second end of the stabilizer to a proximal end of the second fixture member. And, the method includes rotating the first fixture member relative to a rod extending along the spine and causing the second fixture member to rotate therewith through the stabilizer.

These and other features and advantages of the implementations of the present disclosure will become more readily apparent to those skilled in the art upon consideration of the following detailed description and accompanying drawings, which describe both the preferred and alternative implementations of the present disclosure.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

Figure 1:
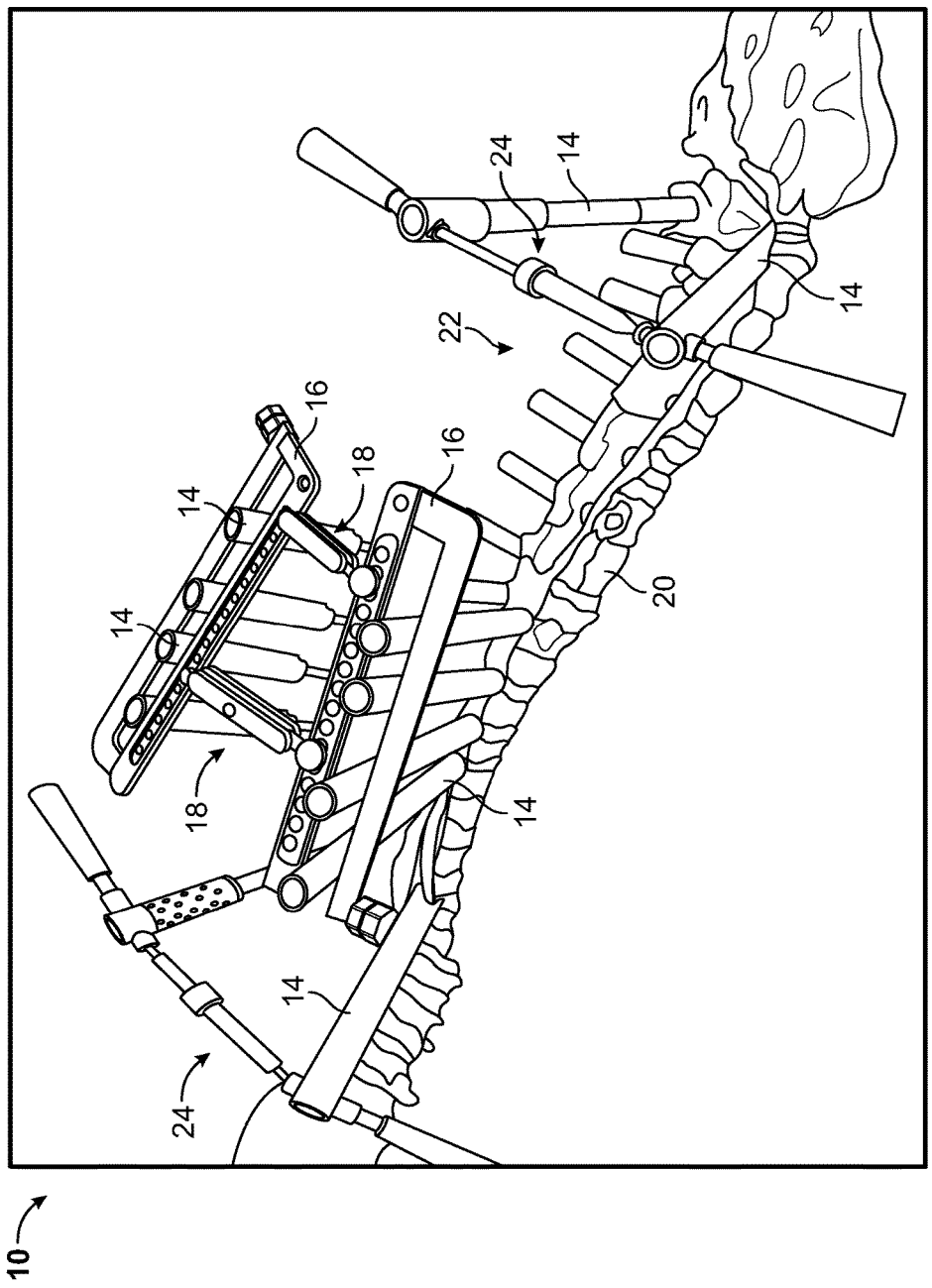
FIG. 1 is a perspective view of a spine derotation system.
Figure 2:
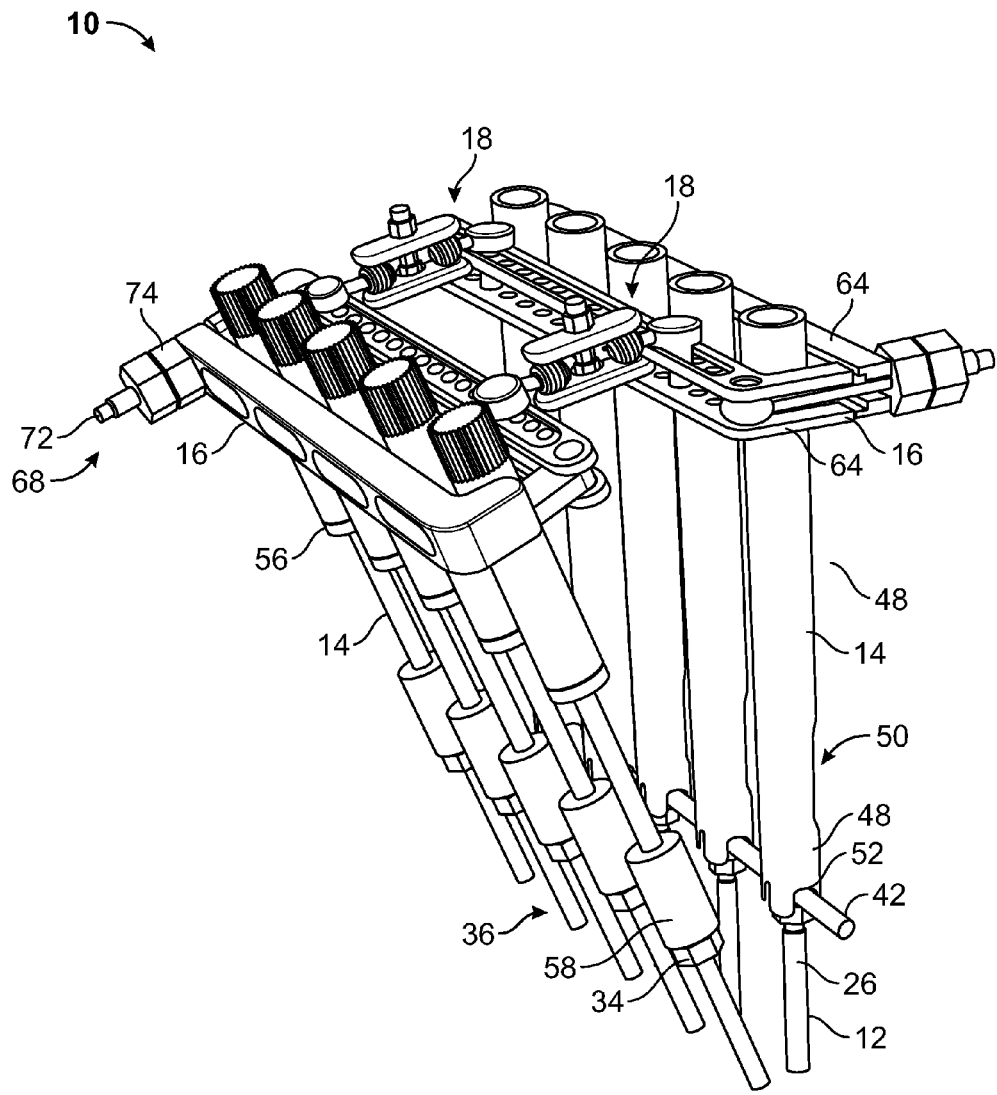
FIG. 2 is a perspective view of a pair of clamp stabilizers used with clamps holding collected fixture members.
Figure 11:
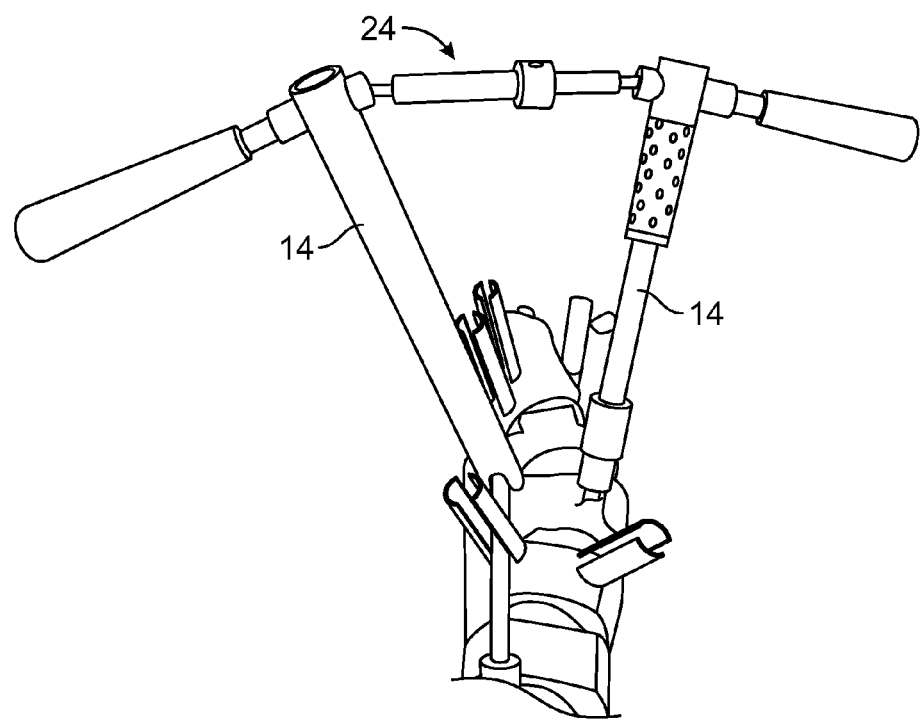

A spine derotation system 10 is shown in FIG. 1. The spine derotation system 10 includes bone fixation elements 12, fixture members 14, clamps 16 and stabilizers. The clamps can collectively lock together multiple proximal ends of bone fixation elements 12 extending from one lateral side of the spine. As shown in FIG. 2, the stabilizers may include clamp stabilizers 18 that are configured to couple together two or more clamps 16 to each other so as to facilitate derotation and alignment of vertebrae 20 of a patient's spine 22. The stabilizers may also include fixture stabilizers 24 that are configured to couple together two fixture members 14 on the same vertebra to facilitate derotation. For example, FIG. 11 shows the fixture stabilizers 24 forming a triangle with the fixture members 14 which are attached to bone fixation elements 12 which are, in turn, attached to a vertebral body or other bone. Although not shown, components of both stabilizer implementations shown here could be employed between multiple fixture members 14 with or without clamps 16.

Figure 12:
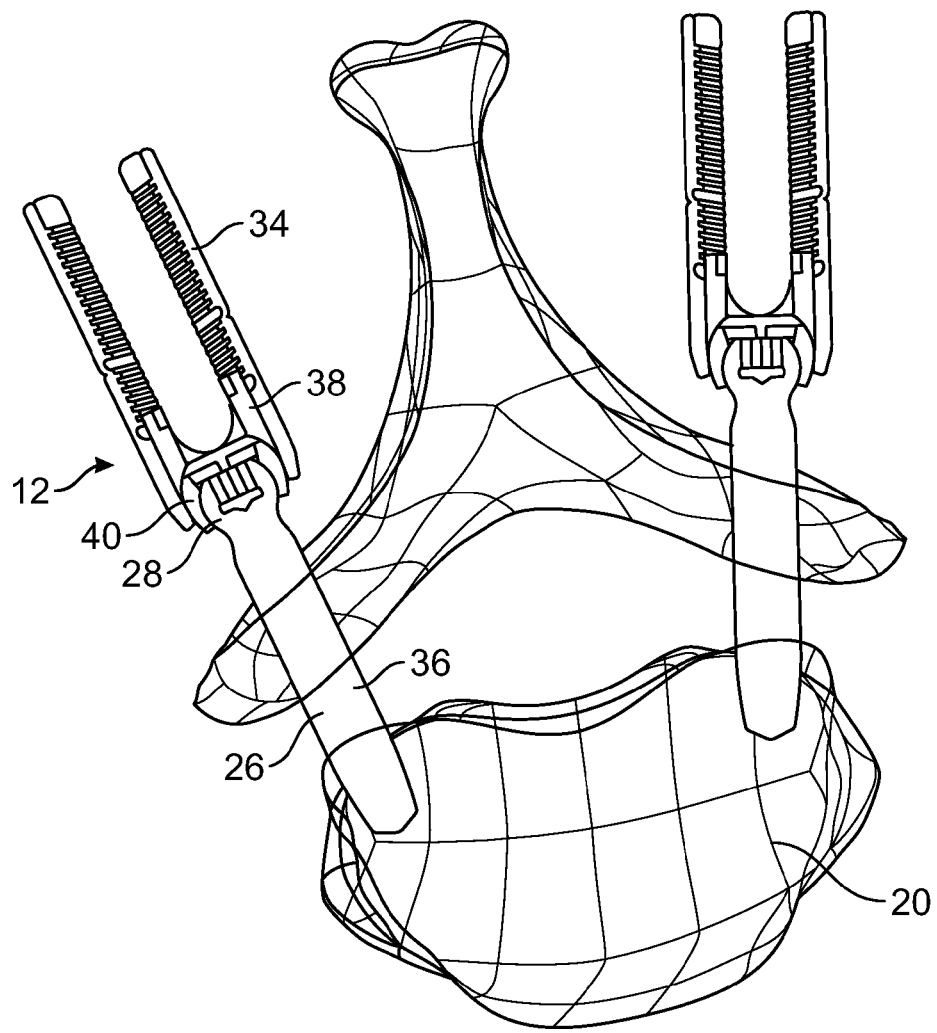
FIGS. 12-20 show a method of derotating a spine using a segmental stabilizer of a spine derotation system.
Figure 13:
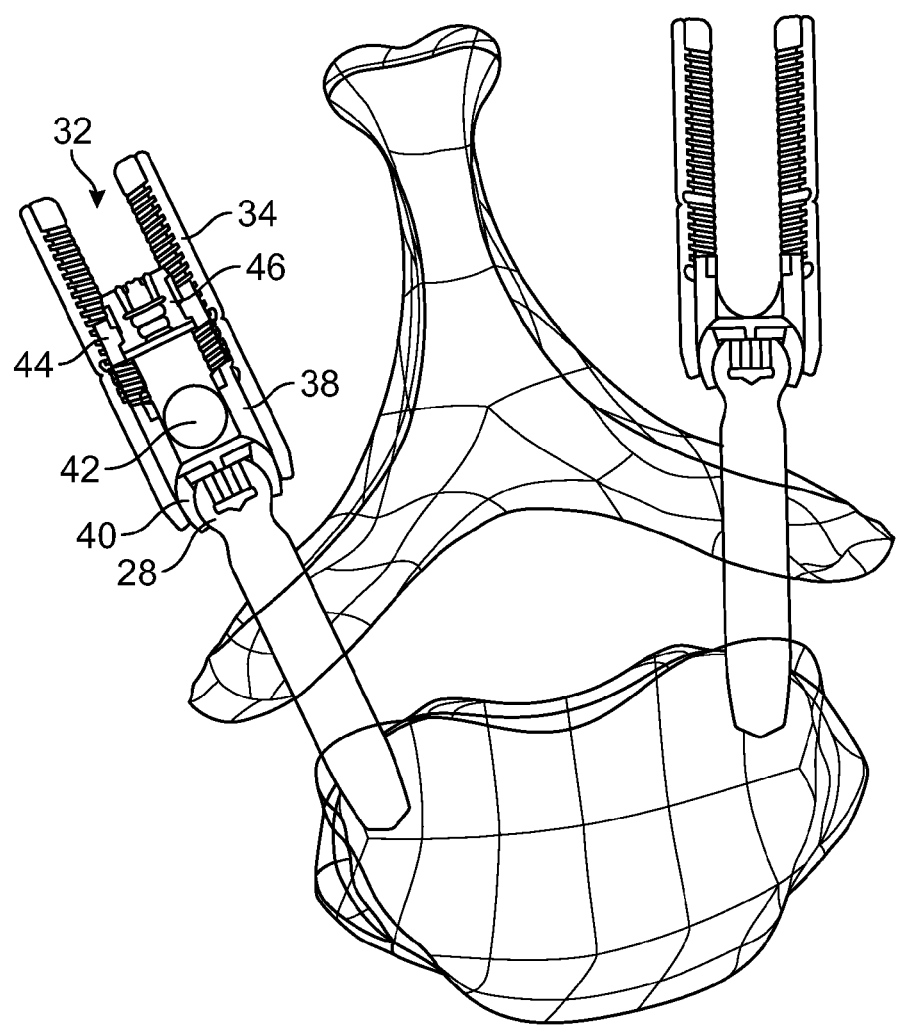

As shown in FIGS. 12-13, the bone fixation elements 12 (or other bone anchors) are configured for insertion into the vertebra 20 from a posterior approach over the spinous processes. The bone fixation elements 12 may include a pedicle screw 36, a locking cap 32, a body 34, a sleeve 38 and a bushing 40.

The pedicle screw 36 includes a shaft 26 and a spherical head 28. The shaft 26 may have an elongate cylindrical shape with threads to allow driving into the bone of the vertebra 20 for firm anchoring. The spherical head 28 is on the proximal end of the shaft 26 and defines a driver opening, such as a hexalobular opening, configured to receive a correspondingly shaped driver. The pedicle screws 12 are secured at diverging angles as they extend posteriorly away from the vertebral body 30.

The body 34 has a cylindrical shape with internal threads extending around an axial opening. The cylindrical shape has an axial split along its top end configured to accept a spine fixation rod 13 therethrough as shown in FIG. 13. Housed within the axial opening at the distal end of the body 34 are the bushing 40 and sleeve 38. The bushing 40 has a frusto-spherical shape that forms a skirt extending around the spherical head 28 of the pedicle screw 36. Adjacent to and above the bushing 40 is housed the sleeve 38. The sleeve also has a split or slot configured to accept the rod 42.

Figure 15:
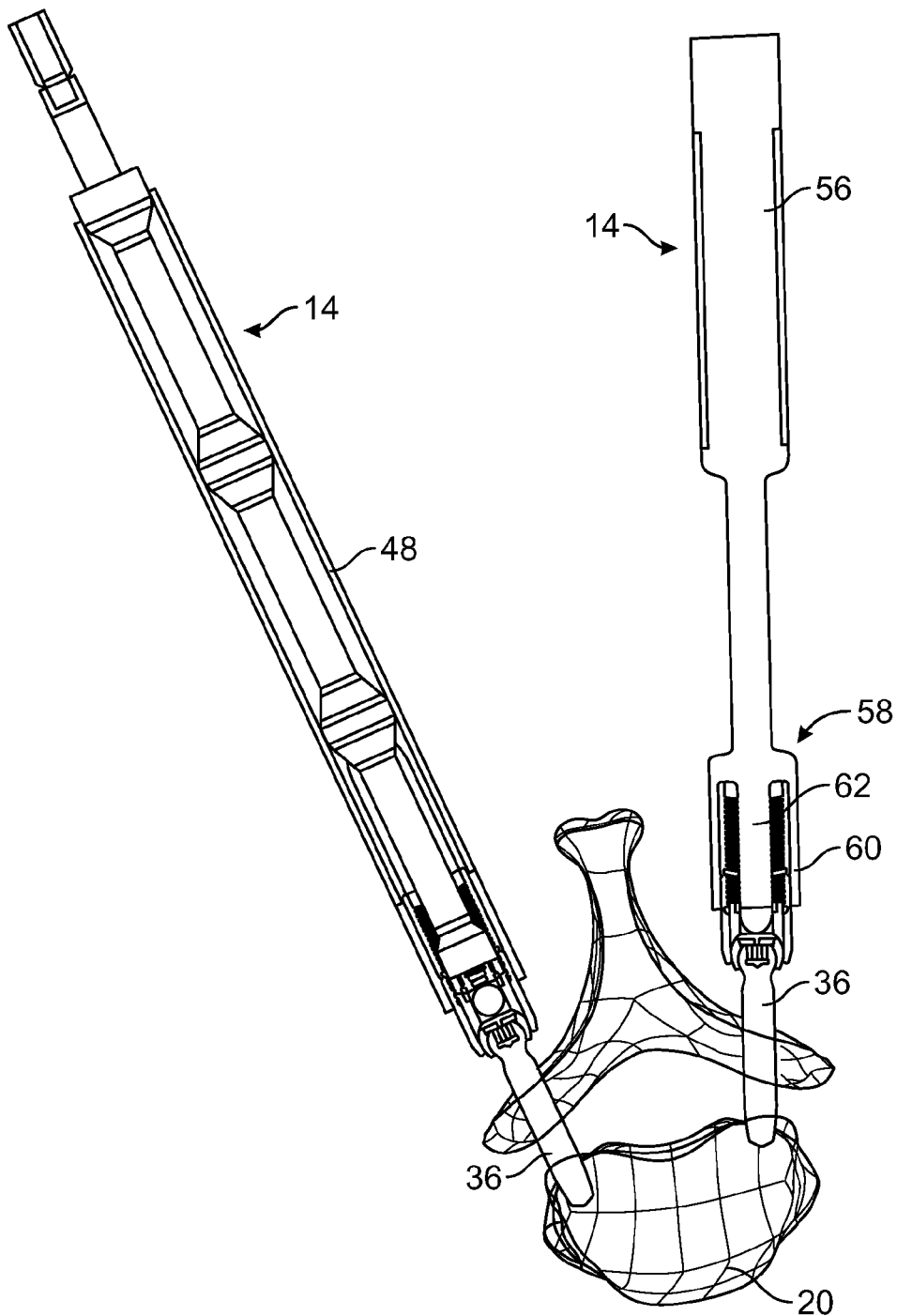
Figure 17:
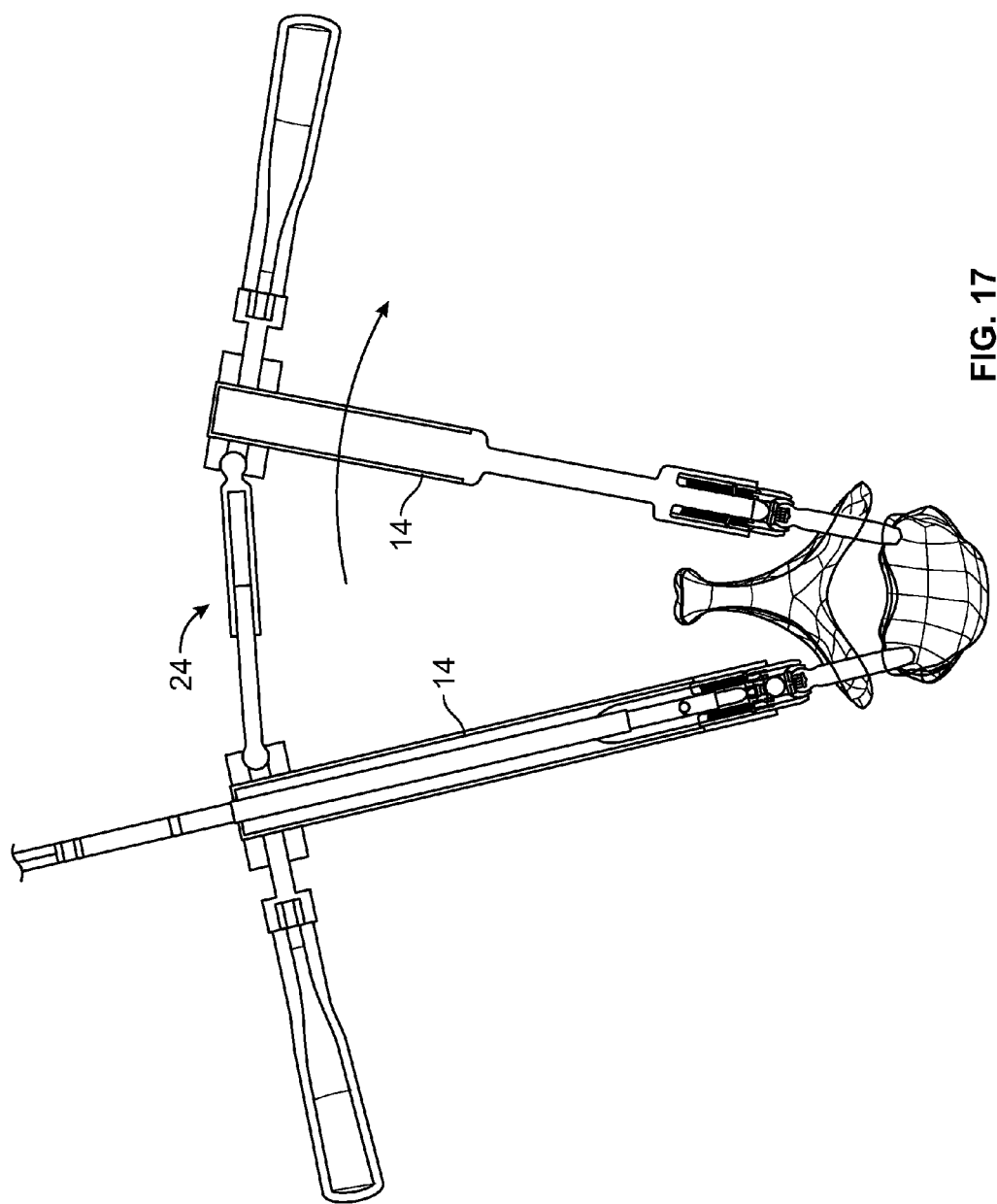

The locking cap 32 includes a threaded outer part 44 and a threaded inner part 46. As shown in FIG. 15, tightening of the outer part 44 with a driver, in a first stage, causes the sleeve 38 to compress against the bushing 40. Compression of the bushing 40 locks the fixation element 12 against poly-axial movement at the spherical head 28 of the pedicle screw 36. The rod 42, however, is still free to slide within the channel formed in the fixation element 12. In a second stage, as shown in FIG. 17, a central driver can then tighten the threaded inner part 46 to lock onto the rod 42 and secure the final range of motion.

Figure 10:
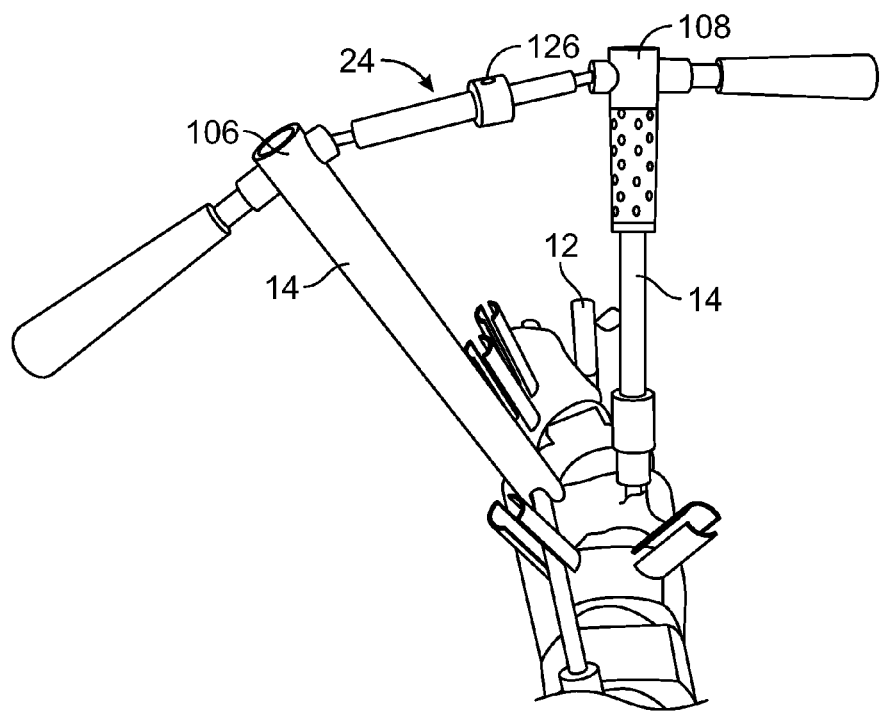
Figure 14:
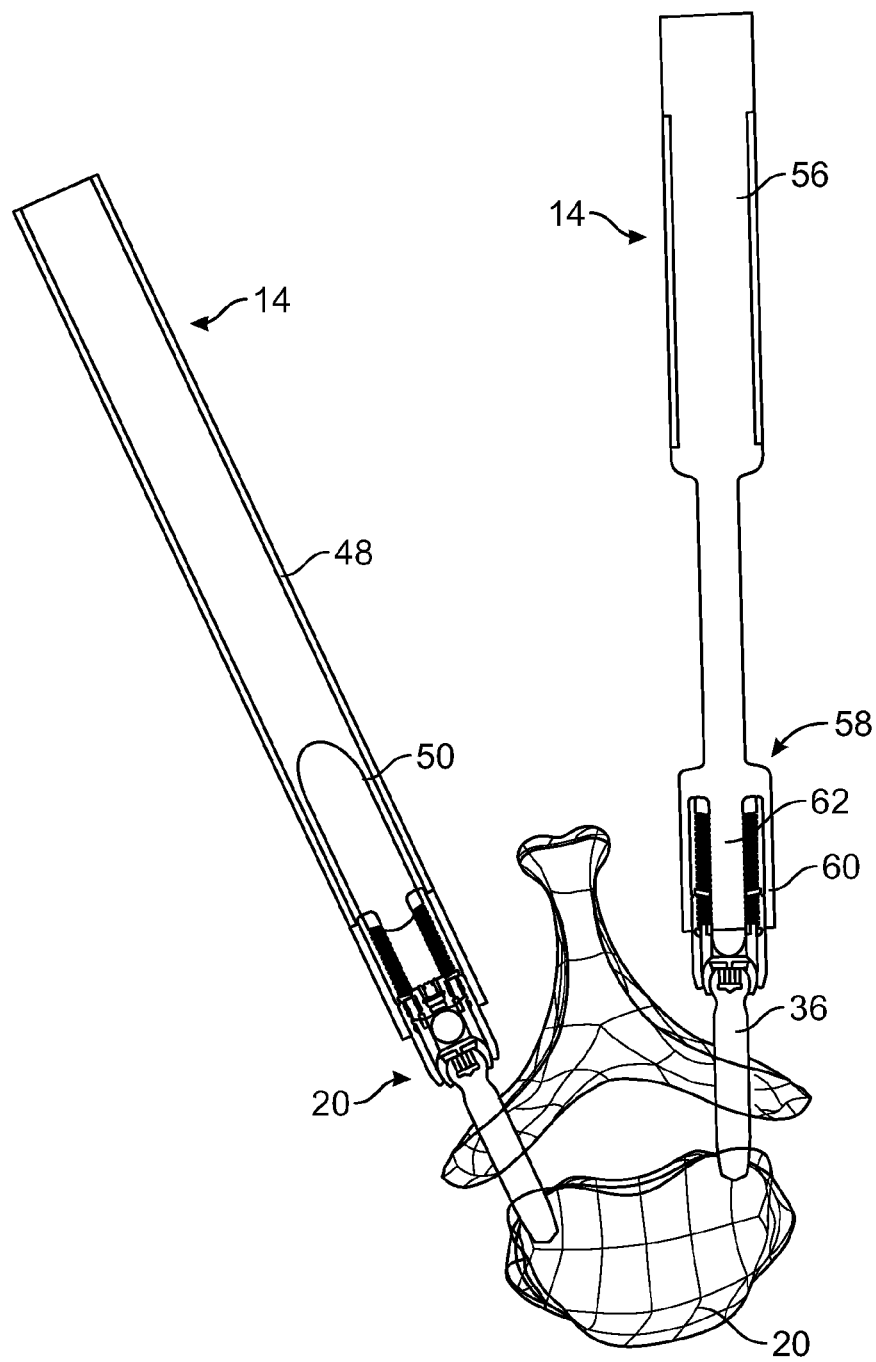

As shown in FIG. 14, the fixture members 14 are generally elongate rods or members that are configured to attach at a distal end to the bone fixation elements 12. A first fixture member 14, shown on the left in FIG. 14, includes an elongate tube 48 which is sized to sleeve over the end of the body 34 of the bone fixation element 12. The elongate tube 48 includes an axial opening, a pair of side openings 50 and a distal notch opening 52. The distal notch opening 52 extends through opposite wall portions of the tube 48 and allow for passage around the rod 42, as shown in FIG. 10.

A second fixture member 14 is shown on the right in FIG. 14 and is not configured to pass any drivers since it will be removed before final locking of the fixation element 12. Instead, the second fixture member 14 includes an elongate body 34 with a proximal handle end 56 and a distal engagement end 58. The distal engagement end 58 includes an outer wall structure 60 that sleeves over the body 34 of the fixation element 12. An inner compression shaft 62 has threads configured to engage and advance along inner threads of the body 34. Advancement compresses the sleeve 38 against the bushing 40, compressing the bushing and locking poly-axial pivoting of the body 34 relative to the pedicle screw 36.

Figure 4:
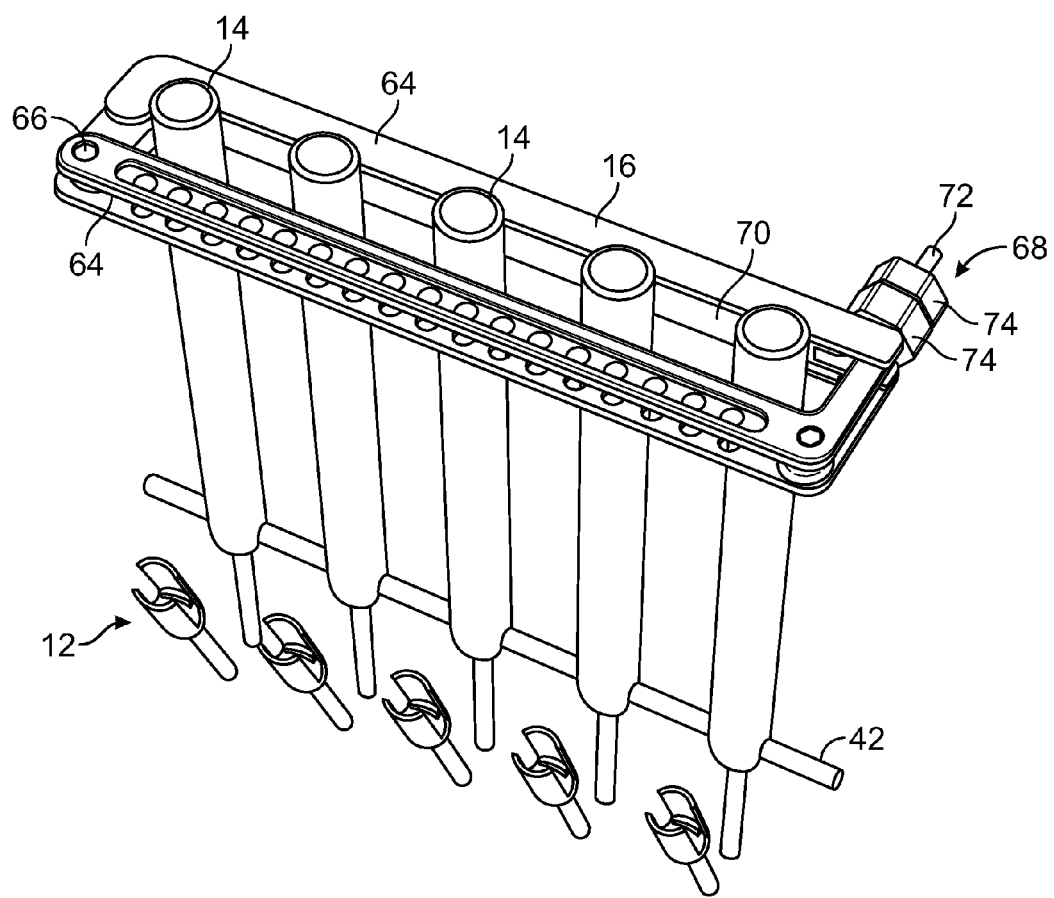
FIG. 4 is a schematic of clamp extend around and locked onto a plurality of fixture members.

Referring now to FIGS. 2 and 4, each of the clamps 16 includes a pair of arm members 64, a pivot pin 66 and a locking assembly 68. Each of the arm members 64 has a pair of members, one short and one long, extending at right angles. The pivot pin 66 attaches the two arm members 64 in a manner to allow their opening to envelope ends of a plurality of adjacent fixture members 14, as shown in FIGS. 1, 2 and 4. The arm members 64 can then be closed at pivot pin 66 to form a rectangular slot within which the proximal ends of the fixture members 14 are held. The arm members 64 may also include pads 70 that extend along internal slots to abut against the fixture members 14 when the arm members are in the closed position.

The clamps 16 may also include the locking assembly 68. The locking assembly 68 includes, for example, a pin 72, as shown in FIG. 2 and one or more rotatable nuts 74. The pin is configured to pivot with respect to the intersection of the long and short members of one of the arm members 64 into a slot defined at the free end of a long member of the other arm member. Once the pin 72 is pivoted into place, the nuts can be advanced on threads to lock the arm members 64 together as shown in FIG. 2.

Figure 3:
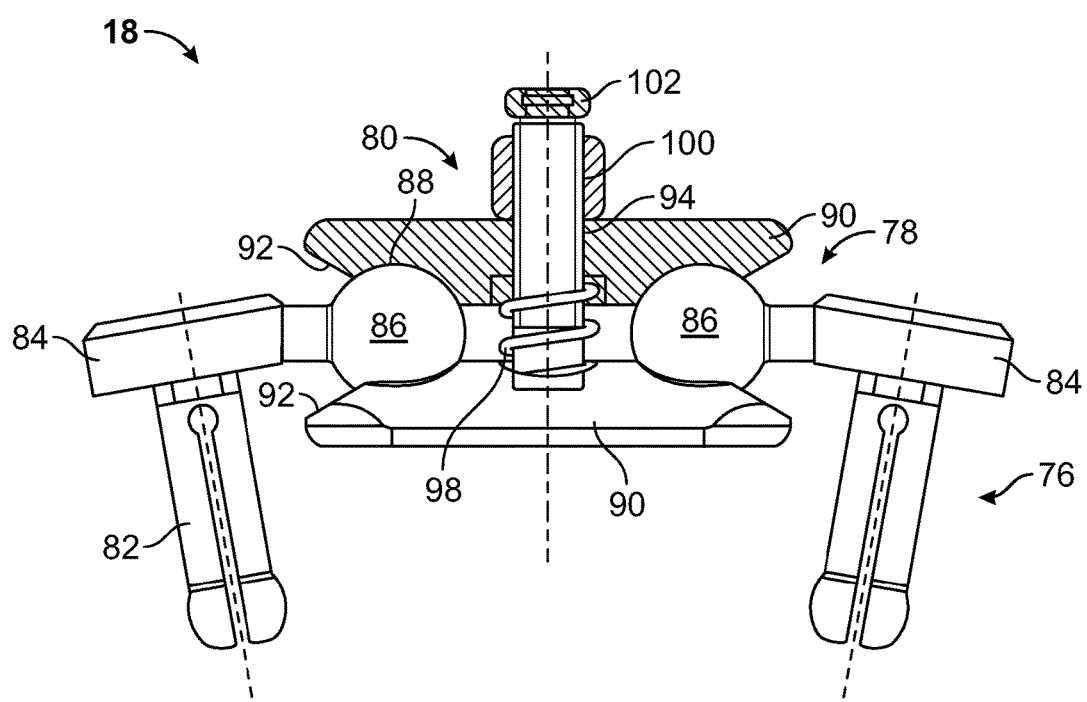
FIG. 3 is a partial cross-section of the clamp stabilizer of FIG. 2.

One or more clamp stabilizers 18 may be used to couple the clamps 16 together, as shown in FIGS. 1 and 2. As shown in FIG. 3, one of the clamp stabilizers 18 includes a connector assembly 76, a pivot joint 78 and a fastening assembly 80. The connector assembly 76 includes a male shaft member 82 and a top plate 84. The male shaft member 82 includes a cylindrical portion and a bulbous, enlarged end portion. Defined through the shaft and enlarged end is a split or channel that ends in a cylindrical opening. The split facilitates deflection of the two portions or arms formed in the male shaft member 82. The top plate 84 is a disc-shaped plate that supports the male shaft member 82.

Figure 5:
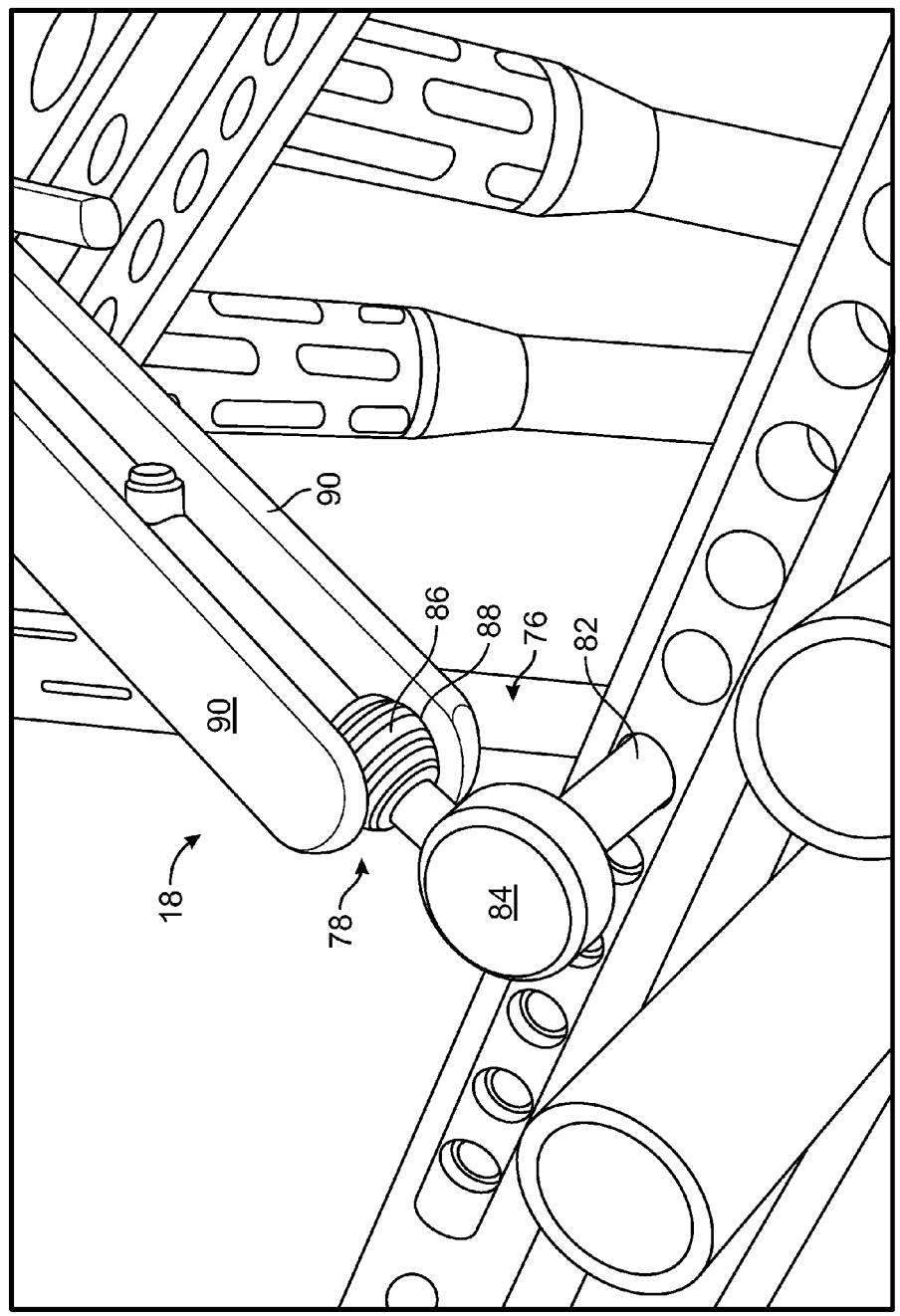
FIG. 5 is an enlarged view of a ball-and-socket joint of a clamp stabilizer.

As shown in FIG. 5, the clamp stabilizers 18 may be attached to the clamps 16 using the connector assembly 76. In particular, the male shaft member 82 is extended through one of a plurality of openings defined along one of the arm members 64. The enlarged end of the shaft member 82 deflects at the split as it passes through the opening in the arm member 64. The shaft member 82 is advanced until the top plate 84 abuts a top surface of the arm member 64 and the enlarged end of the shaft member exits the opening. At this point, enlarged end of the shaft member 82 expands to secure the male shaft member 82 into place. The male shaft member 82 is still free to pivot with respect to the arm member 64.

The male shaft members 82 may be attached at different positions on the clamps 16 and may therefore extend at an angle to the sagittal plane.

The pivot joint 78 includes a ball 86 and a socket 88 configured to receive the ball. The ball 78 is attached via a second shaft to the top plate 84 of the male member at somewhat less than a 90 degree angle. The ball 78 may include serrations or knurls on its outer surface. The socket 88 is defined between a pair of parallel, rectangular plates 90 wherein each of the plates defines a semi-spherical opening. The openings cooperate to form about a ¾ spherical portion of the socket 88. The parallel plates 90 also include sloped sides 92 at their periphery to provide extra clearance and facilitate pivoting of the second shaft with respect to the plates.

The fastening assembly 80 includes center openings 94, a shaft 96, a spring 98, a stop 100 and a cap 102. Each of the parallel plates 90 has a rectangular shape and defines one of the center openings 94, as shown in FIG. 3. The center openings are cylindrical openings configured to receive and pass therethrough the shaft 96. The center openings 94 may also include an expanded diameter portion configured to receive and hold the spring 98.

The shaft 96 transfixes the two plates 90 by passing through the center openings 94. The shaft 96 may be welded or otherwise fixed to the bottom plate 90. The stop 100 is a sleeve configured to slide over an exposed top portion of the shaft 96. The top of the shaft 96 has a reduced diameter and includes threads configured to mate with threads on the cap 102. Attachment of the cap presents an annular stopping surface that serves to block movement of the stop 100. This also blocks movement of the two plates 90 apart from each other. The range of relative movement of the plates 90 is limited so that the space between the plates is less than a diameter of the ball 86. In this manner, the ball 86 is trapped between the plates when the fastening assembly 80 is secured.

Figure 6:
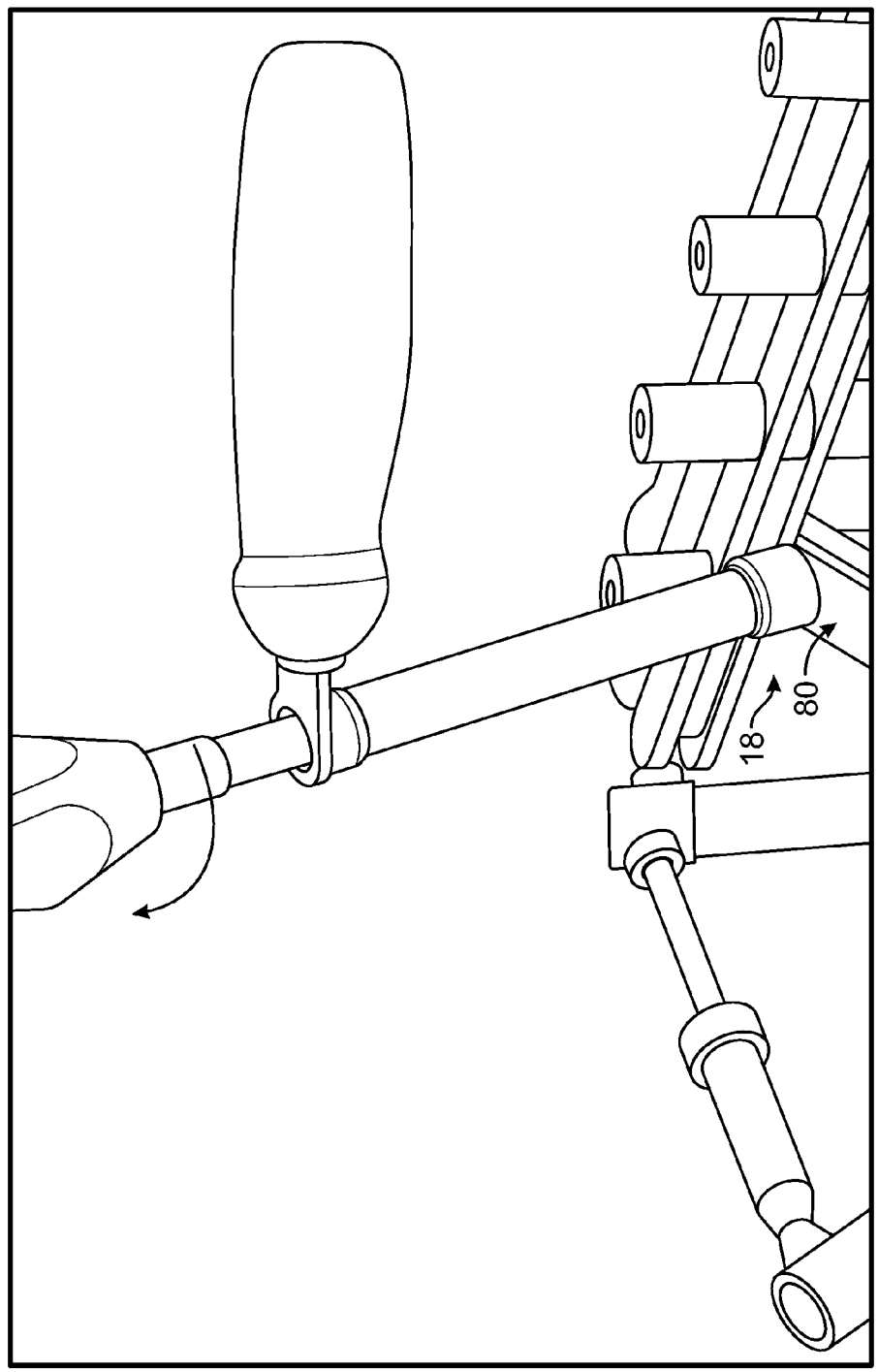
FIG. 6 is a perspective view of a driver for tightening a cap of a clamp stabilizer of FIG. 5.

The spring 98 is a coil spring that extends around the shaft 96 and into the expanded diameter portion of the center openings 94. This traps the ends of the coil spring between the plates 90. The coil spring 98 exerts a bias that urges the plates 90 apart from each other to facilitate pivotal movement of the ball 86 relative to the socket 88. This bias is overcome when the cap 102 is further tightened, such as by the driving tool shown in FIG. 6, squeezing the plates 90 together and locking the ball-and-socket against pivotal movement. The knurls or ridges on the ball 86 may facilitate its locking between the plates.

The components of the clamp stabilizers 18 may vary in size for different desired outcomes or anatomical variability.

Figure 7:
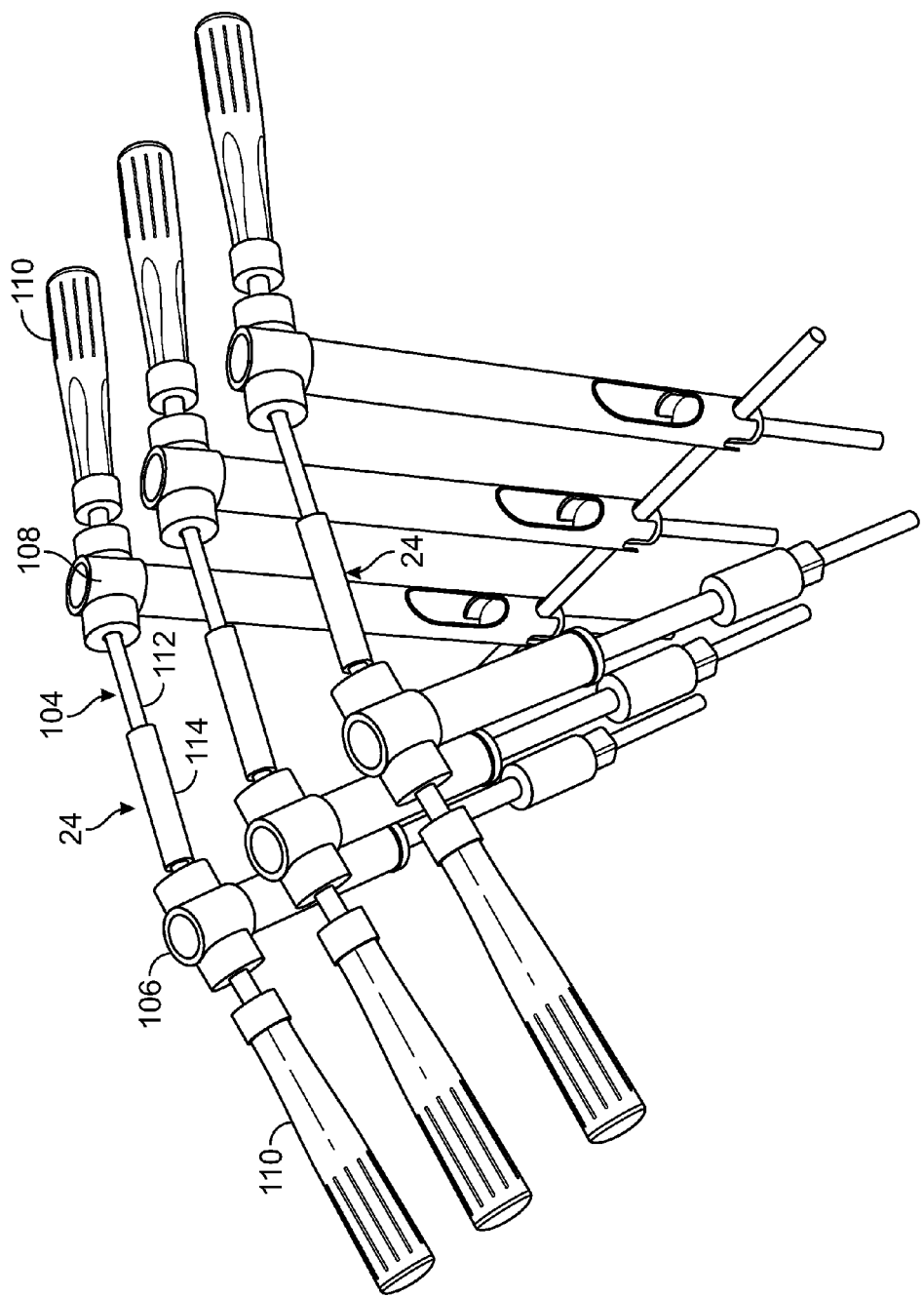
FIG. 7 is a perspective view of plurality of segmental stabilizers used with pairs of fixture members.
Figure 8:
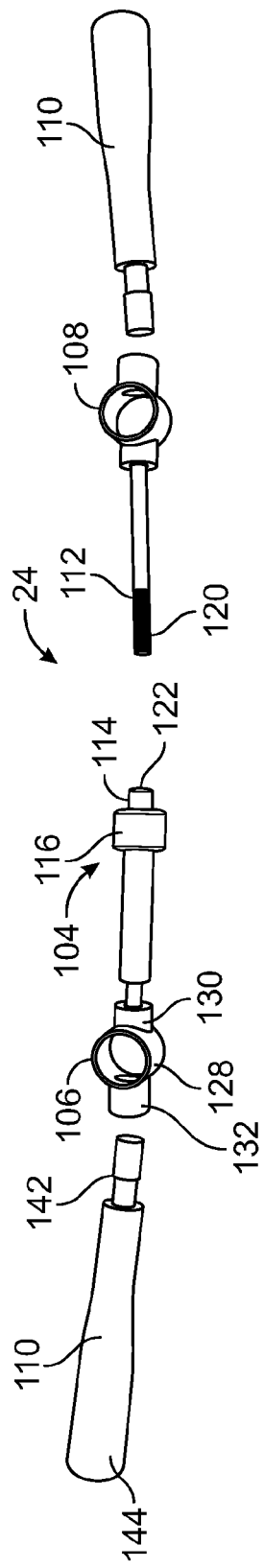
FIG. 8 is an exploded view of a segmental stabilizer.

As shown in FIGS. 1, 7 and 8, the fixture or segmental stabilizer 24 is configured to join two fixture members 14 extending from the same vertebra 20. The fixture or segmental stabilizer 24 includes a central body 104, a first coupling end 106, a second coupling end 108, and a first and second handles 110.

As shown in FIGS. 8 and 9-11, the central body 104 may include a shaft 112, a tube 114 and a locking mechanism 116. The central body 104 of FIG. 18 does not show a locking mechanism. The shaft 112 has a pivot ball 118 at one end and a threaded portion 120 (in the FIG. 18 implementation) at the other end. The tube 114 has a pivot ball 118 at one end and a threaded opening 122 (in FIG. 18) at the other end. The threaded portion 120 may be advanced into the threaded opening 122 to couple the two pivot balls 118.

The locking mechanism 116 of FIGS. 8 and 9-11, rather than the threads, includes an expanded diameter portion 124 on the tube 114 which houses a button 126. The button, when pressed, retracts a pin against a bias and out of engagement with the shaft 112. The shaft 112 may then be slid within the opening 122 to adjust the length of the central body 104. Releasing the button 126 has the reverse effect of engaging the pin with the shaft 112 and locking the length of the central body 104.

Both the threads and locking mechanism 116 may be deployed together for more controlled advancement with locking.

Figure 22:
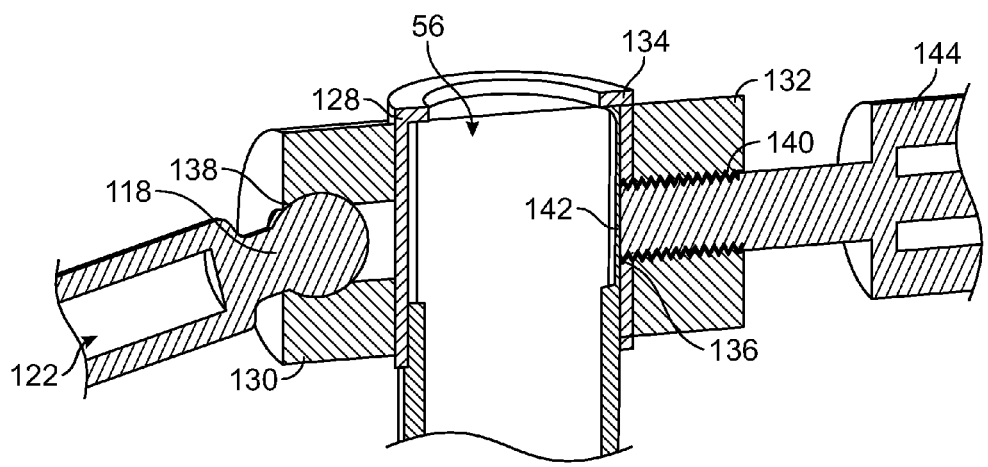
FIG. 22 is a cross-sectional view of a coupling portion of a coupling end of a segmental stabilizer.

As shown in FIG. 22, the coupling ends 106, 108 include a coupling portion 128, a pivot receptacle 130 and a handle receptacle 132. The coupling portion 128 includes a cylindrical sleeve with an axial opening configured to slip over and onto the proximal end of the fixture members 14. The coupling portion includes a side opening 136 which will be explained in more detail below. A top end of the coupling portion 128 includes an inwardly directed flange 134. The flange defines an opening through which a range of driving tools can be used to access bone fixation element 12, as shown, for example in FIG. 17. Also, the inwardly directed flange 134 stops the coupling portion 128 from sliding down the fixture member 14.

The pivot receptacle 130 has a cylindrical shape extending perpendicularly from the axis of the coupling portion 128. The pivot receptacle defines a partially spherical opening or socket 138 that holds and allows pivoting of one of the pivot balls 118. The handle receptacle 132 extends perpendicularly from an opposite side of the coupling portion 128. The handle receptacle 132 defines an axial, threaded opening 140 that is in communication (and aligned with) the side opening 136 in the coupling portion 128.

Each of the handles 110 has a grip portion 144 and a shaft 142 on opposite ends from each other. The grip portion 144 is shaped for easy hand gripping with an expanded diameter and comfort grip. The shaft 142 has a threaded end and is configured to be advanced along the threads defined in the opening 140 of the handle receptacle 132. Full advancement of the threaded shaft 142 extends the shaft through the side opening 136 to lock the coupling portion 128 onto the proximal end of the fixture member 14.

FIGS. 9-20 show a method for attaching and using the spine derotation system 10, and in particular a configuration with a segmental stabilizer 24. FIG. 12 shows placement of the poly-axial screws or fixation elements 12 to the vertebral body of the patient's spine 22. In this initial placement, the spine is rotated such as in a scoliosis condition.

FIG. 13 shows insertion of the rod 42 through the slots defined in the body 34 of the bone fixation element 12. Usually, the rod is first attached on the concave side of the spine 22.

As shown in FIG. 14, the elongate tube 48 of the fixture member 14 is slipped over the body 34 of the bone fixation element 12. Also, the distal engagement end 58 of the second fixture member is sleeved over the body 34. The threads of the compression shaft are advanced within the body to compress the sleeve 30 onto the bushing 40. Compression of the bushing 40 locks the fixation element 12 against poly-axial movement at the spherical head 28 of the pedicle screw 36.

As shown in FIG. 15, a driver is inserted through the elongate tube 48 of the fixture member 14 and drives the outer part 44, in a first stage, causing the sleeve 38 to compress against the bushing 40. Compression of the bushing 40 locks the fixation element 12 against poly-axial movement at the spherical head 28 of the pedicle screw 36. The rod 42, however, is still free to slide within the channel formed in the fixation element 12.

Figure 9:
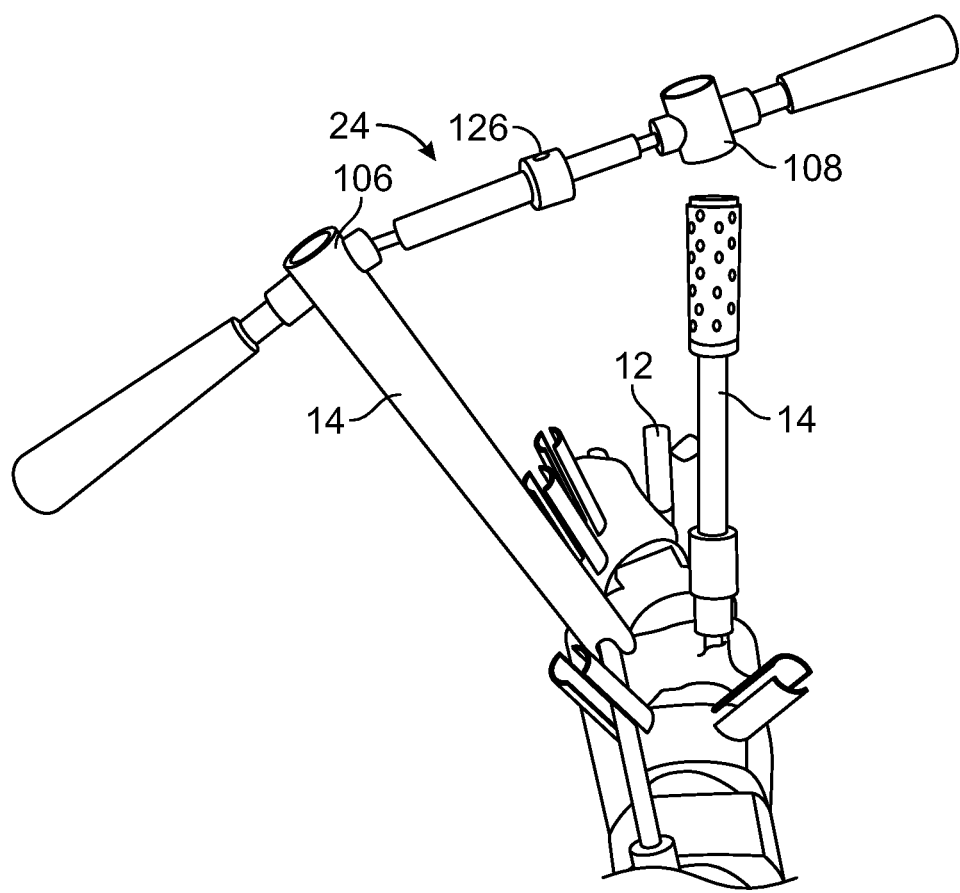
FIGS. 9-11 show a method of coupling a segmental stabilizer to a pair of fixture members.
Figure 16:
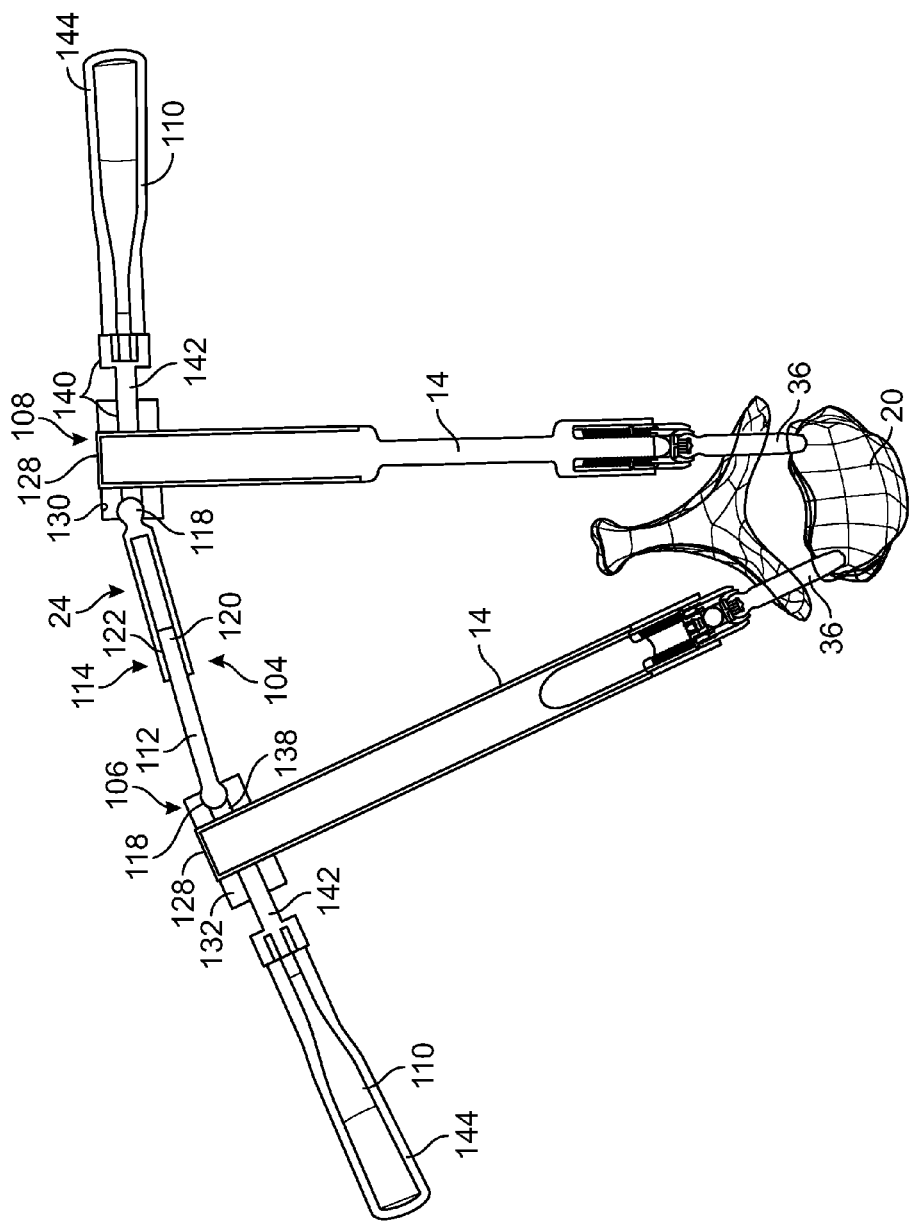

FIGS. 9-11 show coupling portions 128 being sleeved over the proximal ends of the fixture members 14 extending from the same vertebra 20. The coupling portions 128 are rotated at the pivot balls 118 to align the coupling portions 128. Also, as shown in FIG. 16, the shaft 112 may be slid or advanced within the tube 114 to lengthen the central body 104. The button 126, if applicable, is released and the body length is fixed. Sliding of the coupling portions 128 is stopped by the inward flange 134 abutting the top of the fixture members 14.

As shown in FIG. 16, the threaded handle shaft 142 is advanced within the threaded opening 140 in the handle receptacle 132. Advancement is continued until the handle shaft 142 extends through the side opening 136 to abut and lock the coupling portion 128 against the fixture member 14.

Figure 18:
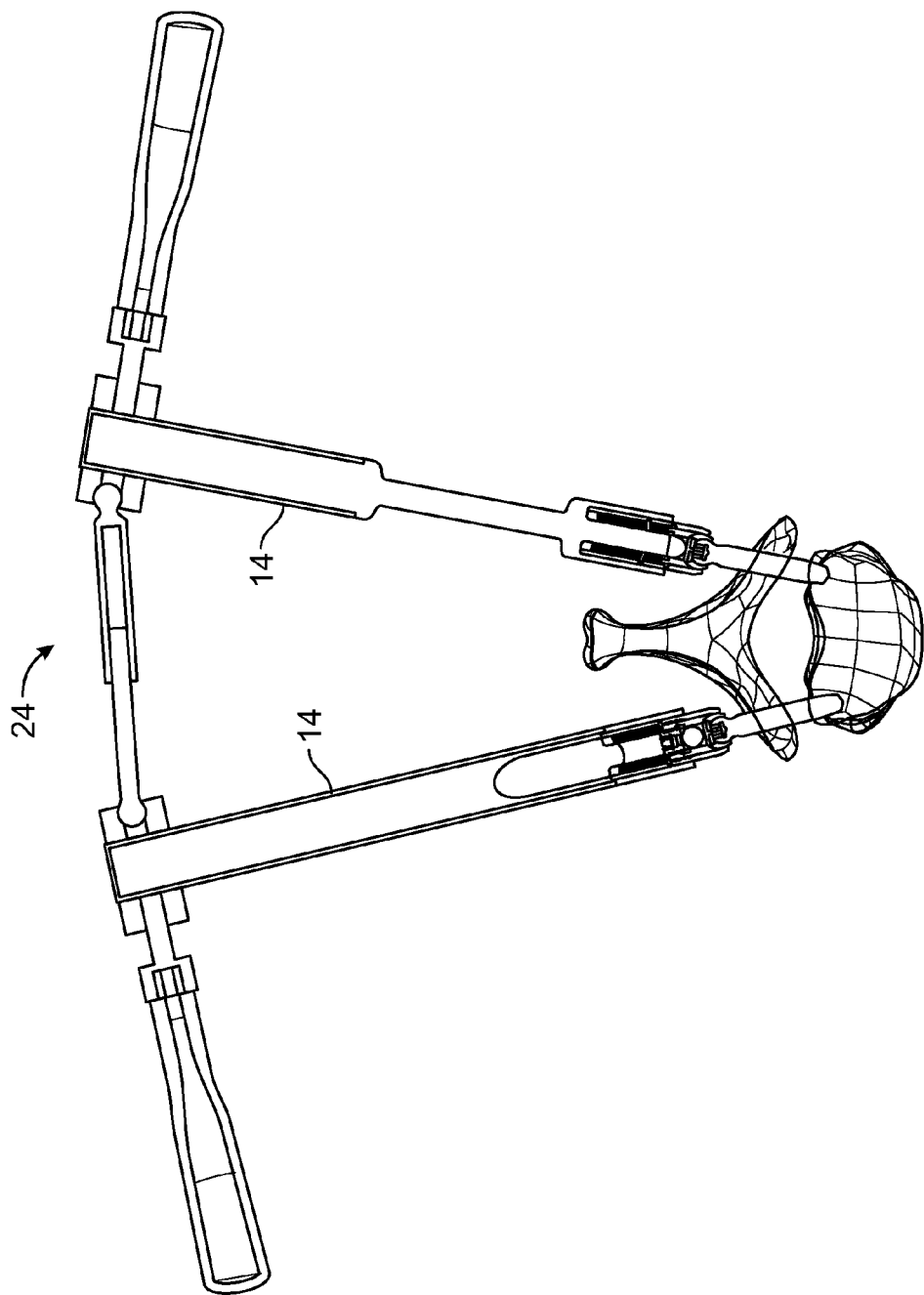

As shown in FIGS. 17 and 18, the handles 110 are used to rotate the assembly about the rod 42 to "de-rotate" the vertebral body 20. Also, a driver is inserted through the opening in the coupling portion 128 and the opening of the elongate tube 48 to drive the inner part 46 of the locking cap 32. This locks the body 34 and fixture member 14 against motion (sliding or rotation) relative to the rod 42 and holds the vertebral body in place.

Figure 19:
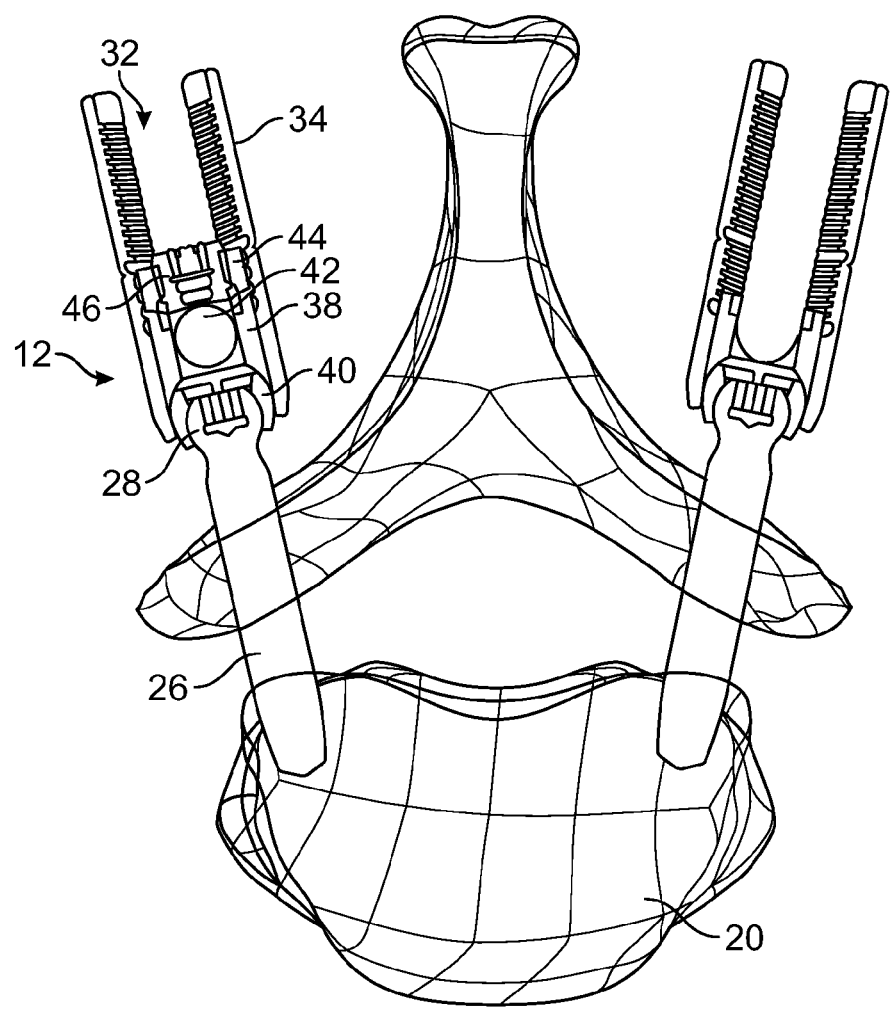
Figure 20:
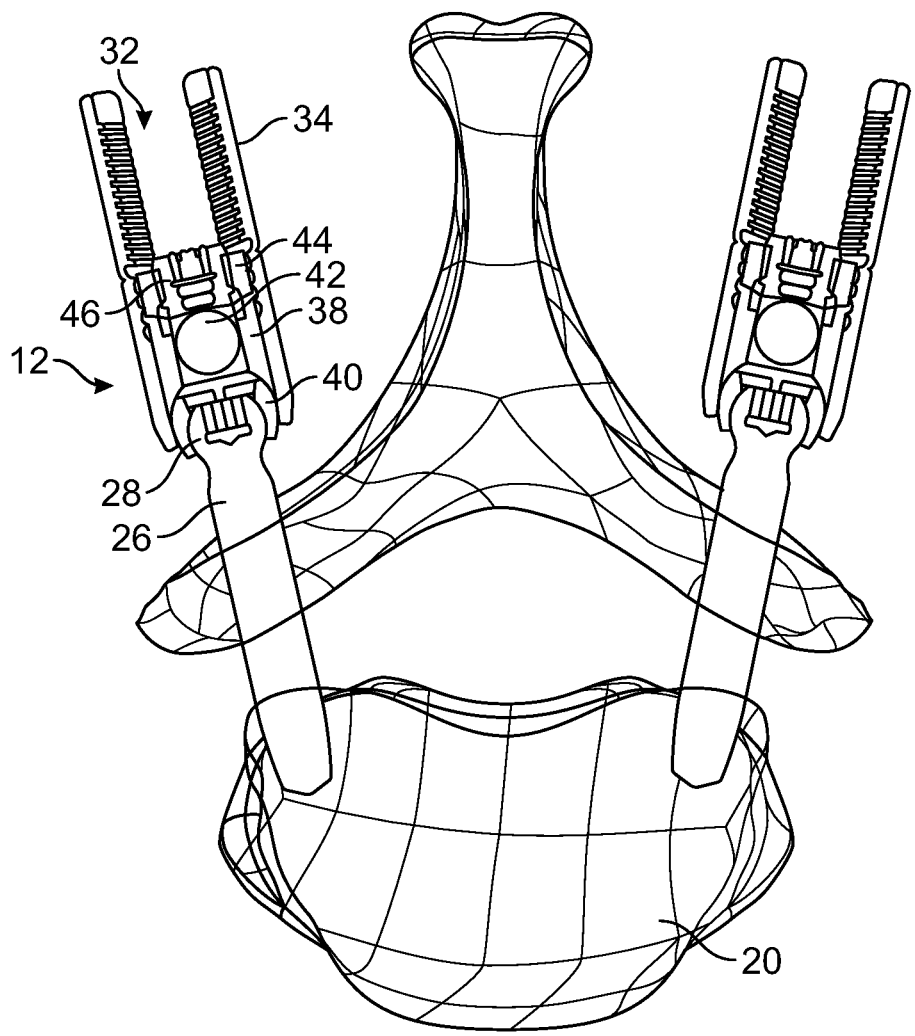

As shown in FIGS. 19 and 20, all of the instruments are removed and the second rod 42 is secured within the body 34 with advancement of the locking cap 32 with inner and outer drivers. This also locks the bushing 40 against the spherical head 28 of the pedicle screw 36. Advantageously, the vertebral body 20 is then secured in the de-rotated position.

Figure 23:
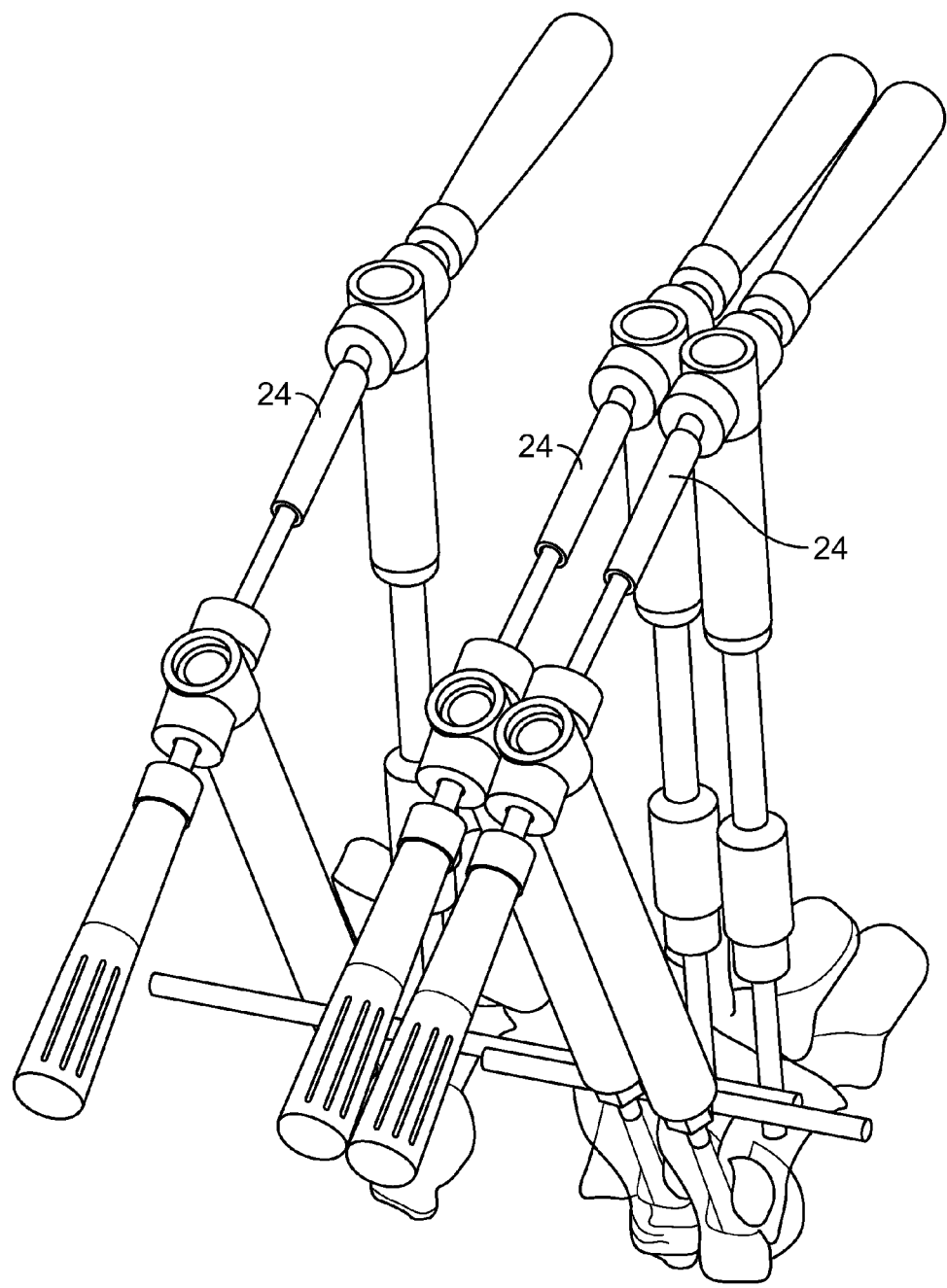
FIG. 23 is a perspective view of several adjacent segmental stabilizers used on a spine.

As shown in FIG. 23, several of the fixture stabilizers 24 can be used in close proximity along the inferior-superior axis of the spine since they do not extend beyond the inferior-superior width of the fixture members 14.

Figure 21:
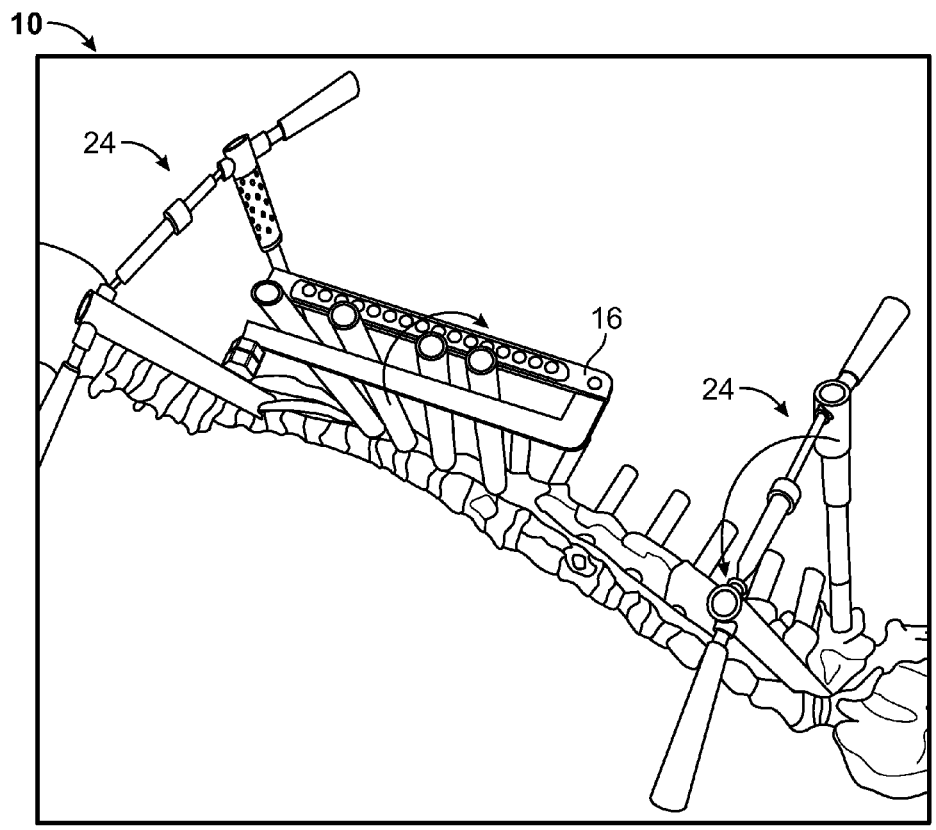
FIG. 21 is a perspective view of both clamp and segmental stabilizers used to derotate a spine.

As shown in FIG. 21, both segmental stabilizers 24 and clamp stabilizers 18 can be employed to de-rotate the spine 22.

A number of aspects of the systems, devices and methods have been described. Nevertheless, it will be understood that various modifications may be made without departing from the spirit and scope of the disclosure. Accordingly, other aspects are within the scope of the following claims.

That which is claimed:

1. A stabilizer for a spine derotation system, the spine derotation system comprising at least a first fixture member and a second fixture member, wherein each of the fixture members includes a distal end configured for attachment to a vertebra and a proximal end configured to extend from the vertebra, the stabilizer comprising:
   a first end member and a second end member each defining a cylindrical sleeve including an elongated central opening for receiving the proximal end of the corresponding first and second fixture members, the first and second end members each including:
   a pivot receptacle on an outer surface of the sleeve defining a cylindrical-shaped body extending perpendicularly from the sleeve, and
   a handle receptacle extending perpendicularly on an opposite side of the sleeve in alignment with the pivot receptacle;
   a body extending between the first and second end members and configured to couple motion of the proximal ends of the fixture members, the body including two members, one configured to slide within the other to allow relative movement between a first and second end of the body along a longitudinal axis of the body, the body pivotably coupled to each of the first end member and the second end member at the corresponding pivot receptacle to allow pivoting movement between the first and second end members and corresponding handle receptacles,
   a first handle configured to fixedly connect to and extend from the handle receptacle of the first end member in a direction opposite the body, a second handle configured to fixedly connect to and extend from the handle receptacle of the second end member in a direction opposite the body, and wherein the handle receptacles of the first and second end members each define a cylindrical-shaped body extending perpendicularly from the sleeve of the corresponding first and second end member, the handle receptacles each including a threaded opening for receiving a shaft of the corresponding first and second handle, the threaded opening aligning with a centerline of the pivot receptacle, wherein the handles extend laterally away from each other.

2. A stabilizer of claim 1, wherein the central opening of the first end member includes a cylindrically-shaped opening configured to fit over the proximal end of the first fixture member.

3. A stabilizer of claim 2, wherein the central opening is sized and configured to allow passage of a driver through the first end member to access a locking cap at the distal end of the first fixture member.

4. A stabilizer of claim 2, wherein the central opening of the second end member includes a cylindrically-shaped opening configured to fit over the proximal end of the second fixture member.

5. A stabilizer of claim 4, wherein the body has an adjustable length.

6. A stabilizer of claim 1, wherein the body is configured to lengthen.

7. A stabilizer of claim 6, wherein the two members of the body include an outer member and an inner member received within the outer member, the inner member configured to slide within the outer member so as to lengthen or shorten the body.

8. A stabilizer of claim 7, wherein the body further includes a lock mechanism configured to stop and allow relative sliding of the inner and outer member, the lock mechanism comprising an expanded diameter portion extending over an outer one of the two members of the body, the expanded diameter portion a release mechanism for engaging a corresponding pin into and out of engagement with an inner one of the two members.

9. A stabilizer of claim 1, wherein the first and second handles are configured to fixedly connect to the first and second end members, respectively, via threads.

10. A stabilizer of claim 1, further including a first fixture member and a second fixture member each of the fixture members including a distal end configured for attachment to a vertebra and a proximal end received within the corresponding first and second end member, wherein the distal end of the first fixture member is configured to attach to a first pedicle screw and wherein the distal end of the second fixture member is configured to attach to a second pedicle screw.

11. A stabilizer of claim 10, wherein the stabilizer, first fixture member and second fixture member are configured to form a triangle when connected together and attached to the vertebra.

12. A stabilizer of claim 10, wherein the first and second fixture members extend away from the vertebra at a diverging angle.

13. A stabilizer of claim 1, wherein the first and second end member include inward flanges extending from central opening of the sleeve configured to stop sliding of the first and second end members relative to the fixture members.

14. A stabilizer of claim 1, wherein the handle receptacles of the first and second end members include a side opening aligned with the threaded opening, the side opening extending from an end of the threaded opening to the central opening, wherein each of the first and second handles includes a shaft including an engagement feature for engaging the threaded opening of the handle receptacle, the wherein full advancement of the shaft extends the shaft through the handle receptacles and into the central opening of the first and second end members and lock the shaft against one of the first or second fixture members.

15. A stabilizer of claim 1, wherein the pivot receptacles each define a cylindrical shaped body extending perpendicularly from the sleeve of the corresponding first and second end member, the pivot receptacles each including a socket for receiving a corresponding pivot ball extending from the body.

16. A stabilizer for a spine derotation system, the spine derotation system comprising at least a first fixture member and a second fixture member, wherein each of the fixture members includes a distal end configured for attachment to a vertebra and a proximal end configured to extend from the vertebra, the stabilizer comprising:

a first end member and a second end member each defining a cylindrical sleeve including an elongated central opening for receiving the proximal end of the corresponding first and second fixture members, the first and second end members each including:

a pivot receptacle on an outer surface of the sleeve defining a cylindrical-shaped body extending perpendicularly from the sleeve, and a handle receptacle extending perpendicularly on an opposite side of the sleeve in alignment with the pivot receptacle;

a body extending between the first and second end members and configured to lengthen and configured to couple motion of the proximal ends of the fixture members, the body including two members, one configured to slide within the other to allow relative movement between a first and second end of the body along a longitudinal axis of the body, the two members of the body including an outer member and an inner member received within the outer member, the inner member configured to slide within the outer member so as to lengthen or shorten the body, the body pivotably coupled to each of the first end member and the second end member at the corresponding pivot receptacle to allow pivoting movement between the first and second end members and corresponding handle receptacles, wherein the body further includes a lock mechanism configured to stop and allow relative sliding of the inner and outer member, the lock mechanism comprising an expanded diameter portion extending over an outer one of the two members of the body, the expanded diameter portion a release mechanism for engaging a corresponding pin into and out of engagement with an inner one of the two members.

17. A stabilizer of claim 16, wherein the central opening of the first end member includes a cylindrically-shaped opening configured to fit over the proximal end of the first fixture member.

18. A stabilizer of claim 17, wherein the central opening is sized and configured to allow passage of a driver through the first end member to access a locking cap at the distal end of the first fixture member.

19. A stabilizer of claim 17, wherein the central opening of the second end member includes a cylindrically-shaped opening configured to fit over the proximal end of the second fixture member.

20. A stabilizer of claim 19, wherein the body has an adjustable length.

21. A stabilizer of claim 16, further including a first fixture member and a second fixture member each of the fixture members including a distal end configured for attachment to a vertebra and a proximal end received within the corresponding first and second end member,
wherein the distal end of the first fixture member is configured to attach to a first pedicle screw and wherein the distal end of the second fixture member is configured to attach to a second pedicle screw.

22. A stabilizer of claim 21, wherein the stabilizer, first fixture member and second fixture member are configured to form a triangle when connected together and attached to the vertebra.

23. A stabilizer of claim 21, wherein the first and second fixture members extend away from the vertebra at a diverging angle.

24. A stabilizer of claim 16, wherein the first and second end member include inward flanges extending from central opening of the sleeve configured to stop sliding of the first and second end members relative to the fixture members.

25. A stabilizer of claim 16, wherein the pivot receptacles each define a cylindrical shaped body extending perpendicularly from the sleeve of the corresponding first and second end member, the pivot receptacles each including a socket for receiving a corresponding pivot ball extending from the body.

* * * * *